United States Patent [19]
Aihara et al.

[11] Patent Number: 5,906,148
[45] Date of Patent: May 25, 1999

[54] MICROTOME HAVING VIBRATION DAMPENING AND MICRO-FEEDING MECHANISM

[75] Inventors: Kaoru Aihara, Saitama-ken; Kentaro Asakura; Soutoku Asano, both of Tokyo; Toichi Imasaka, Chiba-ken; Nobuyoshi Kataoka; Sadao Furusho, both of Saitama-ken; Toshio Sato, Chiba-ken; Yasuhisa Hirohata; Mototugu Yamamoto, both of Tokyo, all of Japan

[73] Assignee: Chuo Precision Industrial Co., Ltd., Tokyo, Japan

[21] Appl. No.: 08/803,423

[22] Filed: Feb. 20, 1997

[30] Foreign Application Priority Data

Jan. 10, 1997 [JP] Japan ..................................... 9-014598

[51] Int. Cl.⁶ ............................... B23Q 1/25; B26D 7/06
[52] U.S. Cl. .................................. 83/72; 83/414; 83/703; 83/915.5
[58] Field of Search ........................... 83/915.5, 72, 703, 83/414

[56] References Cited

FOREIGN PATENT DOCUMENTS

| | | |
|---|---|---|
| 282994 | 7/1970 | Austria . |
| 320308 | 2/1975 | Austria . |
| 397876 | 7/1994 | Austria . |
| 398848 | 2/1995 | Austria . |
| 2321757 | 3/1974 | Germany . |
| 3410831 | 9/1985 | Germany . |
| 434790 | 10/1967 | Switzerland . |
| 1362101 | 7/1974 | United Kingdom . |

*Primary Examiner*—M. Rachuba
*Attorney, Agent, or Firm*—Greenblum & Bernstein P.L.C.

[57] ABSTRACT

The microtome of the present invention includes a base, a knife for cutting a sample, a knife holder fixed on the base and holding the knife, a carrier bar carrying the sample at the leading end thereof and vertically traveling with the trailing end as a fulcrum. A bar traveling mechanism supports and moves the carrier vertically. A transmission lever transmits force to feed the leading end of the carrier bar toward the knife. A support plate is mounted on the base and rotatably supports the transmission lever. A tension spring pulls the carrier bar toward the transmission lever. A lever moving mechanism is in contact with the transmission lever.

11 Claims, 11 Drawing Sheets

MICROTOME HAVING VIBRATION DAMPENING AND MICRO-FEEDING MECHANISM

BACKGROUND OF THE INVENTION

1. Field of the Invention

The present invention relates to a microtome. More particularly, it relates to a microtome suitable for the manufacture of an extra-thin section for an electron microscope.

2. Description of the Related Art

When observing a fine form of a sample using a transmission type electron microscope (TEM), it is the common practice to use the extra-thin section method as a standard technique for the manufacture of the sample.

In order to observe the form of a sample, such as a tissue specimen or a metallic thin piece as a transmission image with the use of a TEM, an electron beam should transmit through the sample. For this purpose, it is necessary to manufacture the sample into an extra-thin section having a thickness within a range of 50 to 100 nm.

One mechanism for finely feeding a sample include mechanically feed based on a combination of a screw, lever and the like. Another method of thermal expansion feed utilizing thermal expansion by an electric lamp or the like.

A thin section cut from a sample should, as described above, preferably have a thickness on the order of a micron or less. During cutting, the micro-feeding accuracy of the sample holder is an important factor. A vibration-free environment is a required prerequisite.

A drawback of the above-mentioned conventional examples is that they do not provide such a vibration-free environment, and are thus not as accurate as possible.

SUMMARY OF THE INVENTION

An object of the present invention is to provide a microtome which solves the drawbacks in the conventional art, reduces the effect of vibration in the micro-feeding mechanism, improves the feed amount accuracy, and produces a thinner sample.

According to the present invention, there is provided a microtome comprising a base; a knife cutting a sample, a knife holder mounted on the base and holding the knife; a carrier bar carrying the sample at the leading end thereof and vertically traveling with the trailing end as a fulcrum; a bar traveling means supporting the carrier bar and causing the carrier bar to vertically travel; a transmission lever transmitting traveling force for feeding the leading end of the carrier bar to the knife; a support plate mounted on the base and rotatably supporting the transmission lever; a tension spring pulling the carrier bar toward the transmission lever; and a lever moving mechanism, in contact with the transmission lever in a slight area, pushing the same.

Since the carrier bar is fed through the transmission lever, it is possible to effectively prevent the carrier bar from being oscillated by vibration from a power source. Moreover, pushing of the transmission lever by the lever moving mechanism through contact in a slight area also permits effective elimination of vibration of the carrier bar. When the carrier bar is fed under the action of pressing by the lever moving means, the force of the tension spring pulling the carrier bar acts against it, and consequently, unnecessary vibration of the carrier bar can be sufficiently prevented. It is thus possible to cut a sample into far thinner sections as compared with the conventional art.

In an embodiment, the lever moving mechanism is provided with a pushing member having a sharp leading end in contact with the transmission lever. Further, the lever moving mechanism may comprise one feed mechanism driving the pushing member in a direction at a certain angle to a direction at right angles to the pushing direction in a plane expanding along the pushing direction of the pushing member; and another feed mechanism driving the pushing member in a direction at a certain angle to the reverse direction to that of the one feed mechanism to a direction at right angles to the pushing direction in that plane, in order to drive the pushing member in the pushing direction in cooperation with the one feed mechanism.

Because the transmission lever is caused to travel by means of the two feed mechanism, the transmission lever can be pushed at an accuracy over that of each feed mechanism.

In another embodiment, the trailing end of the carrier bar should preferably be provided with a wedgeshaped edge coming into contact with the recess of the transmission lever. In this case, vibration in the width direction of the carrier bar can sufficiently be inhibited by forming the edge of the carrier bar with a larger width in a direction at right angles to the feed direction of the carrier bar in a plane expanding along the feed direction than the width of the leading end of the carrier bar, and by making the width of a groove of the transmission lever larger than the width of the leading end of the carrier bar, and smaller than the width of the edge of the carrier bar.

In this embodiment, the tension spring may be arranged at each of the both ends in the width direction on the side of the leading end of the edge of the carrier bar, and the carrier bar may have a straight and sharp tip to be pressed against the recess of the transmission lever by the tension spring. By bringing the transmission lever and the carrier bar at the leading end on a straight line, it is possible to satisfactorily accomplish fine feed while inhibiting vibration in the width direction of the carrier bar, without permitting transmission of vibration of the transmission lever to the carrier bar.

DETAILED DESCRIPTION OF THE PREFERRED EMBODIMENTS

Figure 1:
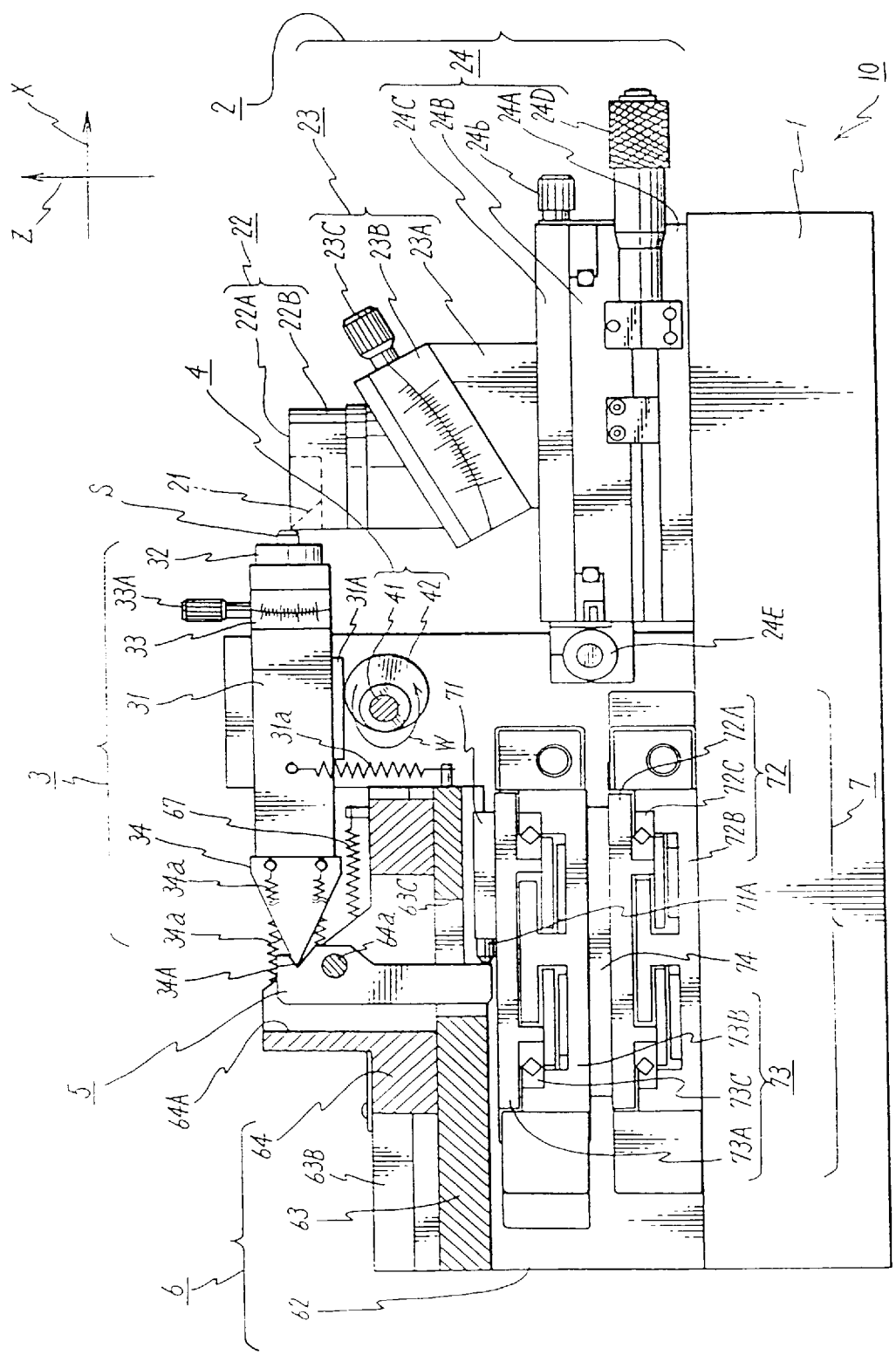
FIG. 1 is a partially cutaway front view illustrating a first embodiment of the present invention.

Now, a first embodiment of the present invention will be described below with reference to FIGS. 1 to 9. As shown in FIG. 1, the microtome of the present invention includes a base 1, a knife 21 for cutting a sample S, a knife support 2 holding knife 21, a carrier bar 3 which holds the sample S at the leading end 34A thereof toward the knife 21 and rotates around the trailing end thereof, and a bar traveling mechanism 4 for rotating carrier bar 3.

The microtome is further provided with a transmission lever 5, which contacts the trailing end of the carrier bar 3 to move the 34A of carrier bar 3 closer to or away from the knife 21, a support plate 6 mounted on the base 1 which rotatably supports the transmission lever 5, a lever moving mechanism 7 which moves the leading end 34A of the carrier bar 3 in units of a micro-distance responsive to the transmission lever 5, and a controller 8 which controls operations of these parts.

The carrier bar 3 includes a square-pole-shaped bar body 31 arranged in the X-axis direction, a sample holder 32 attached to the leading end 34A of the carrier bar 3 directed toward the side of the knife support 2 (right side in FIG. 1) which holds the sample S, a slant stage arranged between the sample holder 32 and an end of the bar body 31, and an edge 34 which is attached to, and biased against, a transmission section 52 of transmission lever 5. In the above description, the X-axis direction is the direction in which the sample S is moved downwards and away from knife 21 responsive to lever moving mechanism 7. Specifically, the direction in which a pushing member 71 of the lever moving mechanism 7 (described below) pushes the transmission lever 5 (right-left direction in FIGS. 1 and 2).

Figure 3:
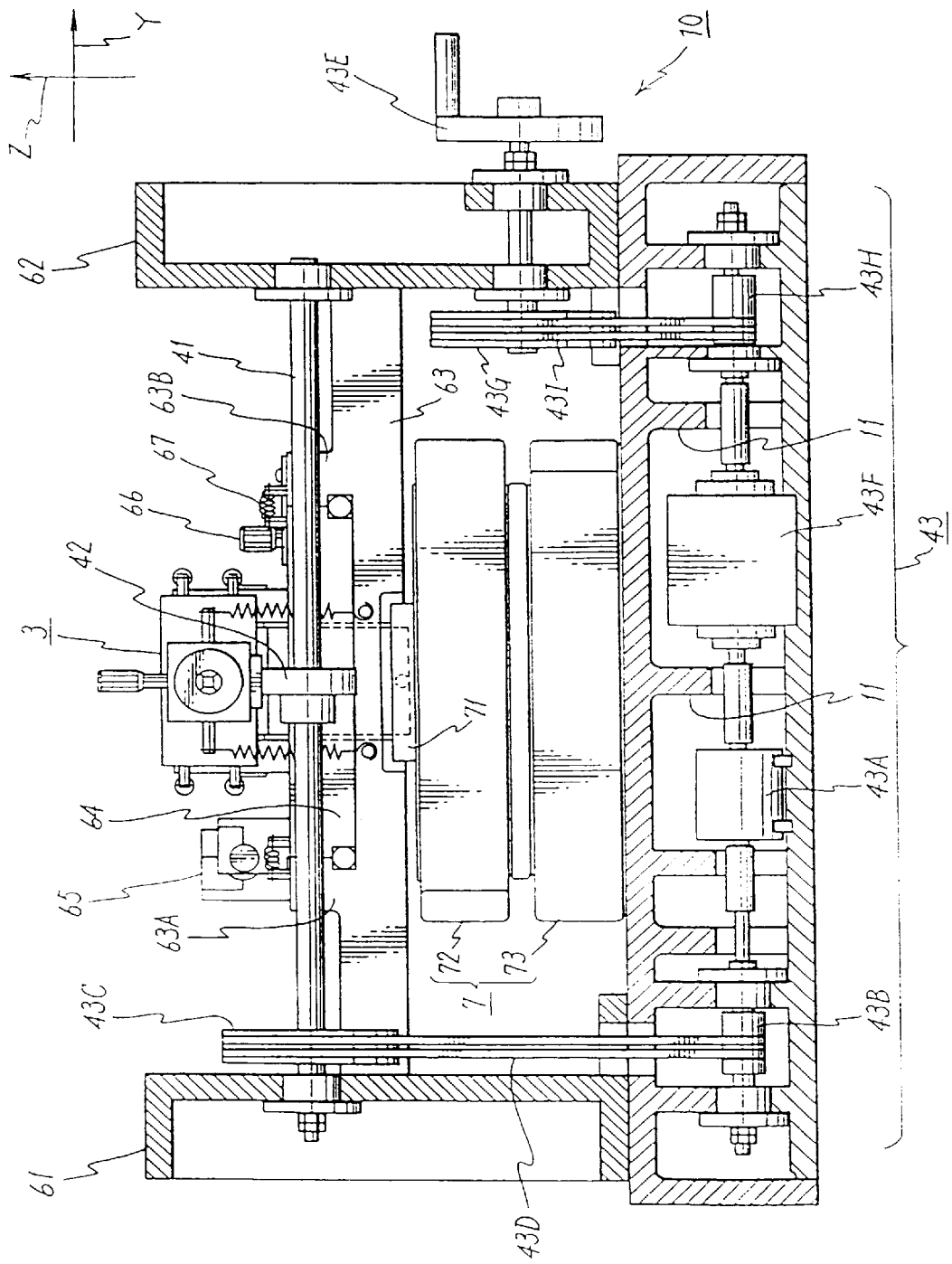
FIG. 3 is a partially side view of the microtome shown in FIG. 1 with portions cut away to show the inner mechanism of the microtome.

For purposes of reference, the Y-axis direction is perpendicular to the X-axis direction in the same plane as that of the X-axis direction (right-left direction in FIG. 3). The Z-axis direction is perpendicular to the plane containing both the X-axis direction and the Y-axis direction (the plane of the page in FIGS. 1 and 3).

For the bar body 31 to be rotatable about its leading end 34A, the leading end 34A is formed into a wedge-shaped. This leading end 34A contacts a V-shaped groove formed along the Y-axis direction on the transmitting section 52 of the transmission lever 5. The entire carrier bar 3 rotates around the Y-axis. Four tension springs 34a connect the leading end 34A and the transmitting section 52 of the transmission lever 5, pulling the entire carrier bar 3 toward the side of the transmission lever 5. The tension springs 34a maintains the contact between the leading end 34A of the edge 34 of the carrier bar 3 and the transmitting section 52 of the transmission lever 5. This eliminates any problems caused in the X-axis direction of the carrier bar 3 during rotation. The other ends of the tension springs 34a are connected to a stage 64 of the transmission lever 5.

It is also necessary to prevent vibration of the sample holder 32 in the Y-axis direction thereof upon rotation of the carrier bar 3. For this purpose, the leading end 34A of the edge 34 has a prescribed width in the Y-axis direction (more specifically, within a range of from about ½ to ⅓ of the length of the carrier bar 3 in the X-axis direction). As a result, the leading end 34A comes into contact with the transmission lever 5 over the entire width thereof, thus eliminating vibration of the sample holder in the Y-axis direction (see FIG. 2).

The bar body 31 of the carrier bar 3 has a contact member 31A under the middle portion thereof. This contact member 31A contacts an eccentric cam 42 of bar traveling means 4, thereby rotating carrier bar 3, with the tip of the edge 34 acting as the pivot point. This contact member 31A is made of a smooth material having a low frictional resistance to minimize displacement in the X-axis direction of the carrier bar 3 due to frictional engagement with the rotating eccentric cam 42.

Two tension springs 31a pull the leading end 34A of the carrier bar 3 toward the eccentric cam 42 springs 31a maintain contact between the contact member 31A and the eccentric cam 42, and prevent any gap from forming between the eccentric cam 42 and the carrier bar 3 during rotation of the eccentric cam 42.

A sample holder 32 is provided through a slant stage 33 on the rotating end side of the bar body 31. This sample holder 32 holds a sample S with the leading end 34A thereof directed toward the knife 21. The slant stage 33 freely adjusts the cutting angle of the sample S during cutting, thus permitting adjustment of the inclination angle with respect to the Y-axis direction. The reference numeral 33A represents an adjusting knob for fine adjustment of the slant stage 33.

The bar traveling means 4 includes a rotation shaft 41 provided rotatably in the Y-axis direction on side walls 61 and 62 of the support plate 6 (described below). The eccentric cam 42 is mounted on the rotation shaft 41 offset from the center axis of the rotation shaft 41. A driving mechanism 43 rotates the rotation shaft 41.

As shown in FIG. 3, this driving mechanism 43 is mounted in the base 1. More specifically, it includes main pulley 43B driven by a driving motor 43A, a sub-pulley 43C mounted coaxially on the rotation shaft 41, and a driving belt 43D for transmitting the rotation force from the main pulley 43B to the sub-pulley 43C.

In the construction as described above, driving motor 43A rotates the eccentric cam 42 through the rotation shaft 41. Movement of eccentric cam 42 rotates the carrier bar 3. The rotation shaft 41 rotates in the direction of the arrow W in FIG. 1. Displacement in the X-axis direction is thereby greatly minimized.

The driving mechanism 43 has a manual handle 43E. Manually rotation of manual handle 43E rotates eccentric cam 42. This manual handle 43E rotates a changeover clutch 43F directly connected to the driving shaft of the driving motor 43A through a main pulley 43G, a sub-pulley 43H and a driving belt 43I.

A changeover clutch 43F switches between connecting and disconnecting the driving shaft of the driving motor 43A and manual handle 43E. During usual driving of the driving motor 43A, the manual handle 43E is disconnected from motor 43A. When a user wants to manually rotate carrier bar 3, an external operation (for example, a changeover instruction signal from the controller 8) connects the changeover clutch 43F between the driving shaft of the driving motor 43A and the manual handle 43E. Rotational force applied to the manual handle 43E is thus transmitted to the eccentric cam 42. At this point, the driving motor 43A is not operative.

Now, the transmission lever 5 will be described below. As shown in FIG. 5(A), the transmission lever has a holding section 51, a transmitting section 52 and a contact section 53. Among these sections, the holding section 51 is a through-hole. A supporting shaft 64a rotatably held on a transmission lever stage 64 of the support plate 6 (described later) is inserted into section 51. The supporting shaft 64a is aligned with the Y-axis direction. The transmission lever 5 is rotatably held by the transmission lever stage 64 around the Y-axis direction by the holding section 51. The transmitting section 52 is a V-shaped groove which contacts the leading end 34A of the edge 34 of the carrier bar 3. This groove is formed in parallel with the inserting direction of the through-hole of the holding section 51. The contact section 53 is the position at which the pushing member 71 of the lever moving mechanism 7 comes into contact. Assisted by these components, the transmission lever 5 transmits a pushing force to the carrier bar 3 in units of a micro-distance imparted by the lever moving mechanism. Carrier bar 3 responds by moving in the X-axis direction by this distance. A V-shaped groove or a slight recess may be provided to hold the above-mentioned contact section 53 in contact with the pushing member 71.

In this transmission lever 5, if the distance between the transmitting section 52 and the holding section 51 is L1, and the distance between the transmitting section 52 and the contact section 53 is L2, then L2 is set to a value between four to five times as large as L1. Therefore, when pushing force is imparted by the lever moving mechanism 7, a micro-displacement distance 1/5 to 1/4 the displacement distance given to the transmission lever is transmitted to the carrier bar 3, such that carrier bar 3 can be positioned along the X-axis direction with a high accuracy. It is not always necessary to limit the ratio L2/L1 within the abovementioned range: setting a higher ratio permits movement in smaller units of micro-distance.

In this embodiment, the transmitting section 52 and the contact section 53 of the transmission lever 5 are provided at the opposite ends of the transmission lever 5 with the holding section 51 in between. In the transmission lever 5A shown in FIG. 5(B), the transmitting section 52A and the contact section 53A may be provided on the same side relative to the holding section 51A. In such a case, if the distance between the transmitting section 52A and the holding section 51A is L1, and the distance between the transmitting section 52A and the contact section 53A is L2, by setting L1:L2 equal to the ratio for the transmission lever 5, the transmission lever 5A exhibits the same functions as those of the transmission lever 5. In this transmission lever 5A, however, pushing force is imparted to the contact section 53A in a direction reverse to that in the transmission lever 5.

Now, the support plate 6 will be described below. The support plate 6 includes a pair of side walls 61 and 62 (the side wall 61 is omitted in FIG. 1) provided upright oppositely with the lever moving mechanism 7 on the base 1. An erection stand 63 installed on these side walls 61 and 62 is located substantially directly above the lever moving mechanism 7. Transmission lever stage 64 moves back and forth in the X-axis direction on the erection stand 63.

The side walls 61 and 62 are mounted on the base 1. The erection stand 63 and the rotation shaft 41 of the bar traveling means 4 are provided between these side walls 61 and 62.

On the erection stand 63, guide rails 63A and 63B are provided along the X-axis direction on the upper surface thereof. A transmission lever stage 64 are engaged slidably along the guide rails 63A and 63B. A through-hole 63C is provided in the erection stand 63 at a position corresponding to the transmission lever 5 held on the transmission lever stage 64. Pushing force is imparted from the lever moving mechanism 7 to the transmission lever 5 as inserted in this through-hole 63C.

Figure 2:
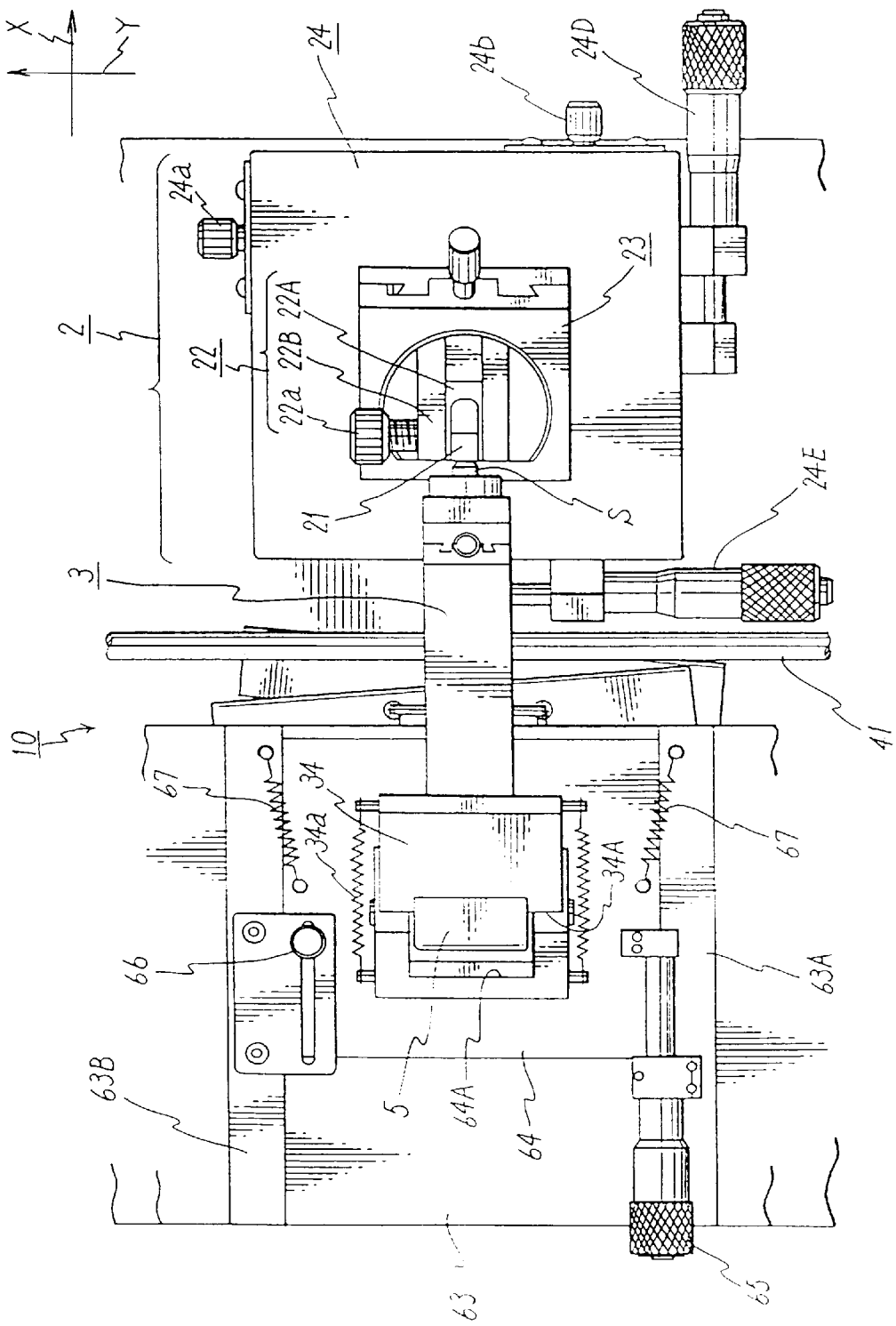
FIG. 2 is a plan view of the partially omitted microtome shown in FIG. 1.

On the transmission lever stage 64, a through-hole 64A is formed substantially at the center as shown in FIG. 2. The transmission lever 5 is held in the state by a support shaft 64a rotatably provided in the Y-axis direction. The transmission lever 5 moves with sliding of the transmission lever stage 64.

Between the transmission lever stage 64 and the erection stand 63, there is provided an adjusting knob 65 which slides the transmission lever stage 64 along the X-axis. A stop screw 66 fixes the transmission lever stage 64. Because this adjusting knob 65 has a screw mechanism which imparts a moving force to the transmission lever stage 64, a tension spring 67 is provided to the transmission lever stage 64 to prevent backlash. In this embodiment, the tension spring 67 provides tension to the transmission lever stage 64 in the right-hand direction in FIG. 1, although it may be provided in the left-hand direction.

The base 1 is an enclosure made of a metal in the form of a casting having an upper horizontal surface. Almost all the components described above are mounted on the horizontal surface. Base 1 also has a built-in driving mechanism 43 of the bar traveling means 4.

A number of ribs 11 extend vertically from the upper surface of the inside of the base 1 to the lower surface thereof to support the weight and arrangement of the components to be mounted on the base 1. Ribs 11 also reduce vibration caused by the components mounted on the base 1.

The knife 21 is made preferably of glass, diamond or sapphire. The knife edge has a cutting angle of 40 to 60°, and is mounted on the knife holder 22 with the edge directed upward.

Figure 4:
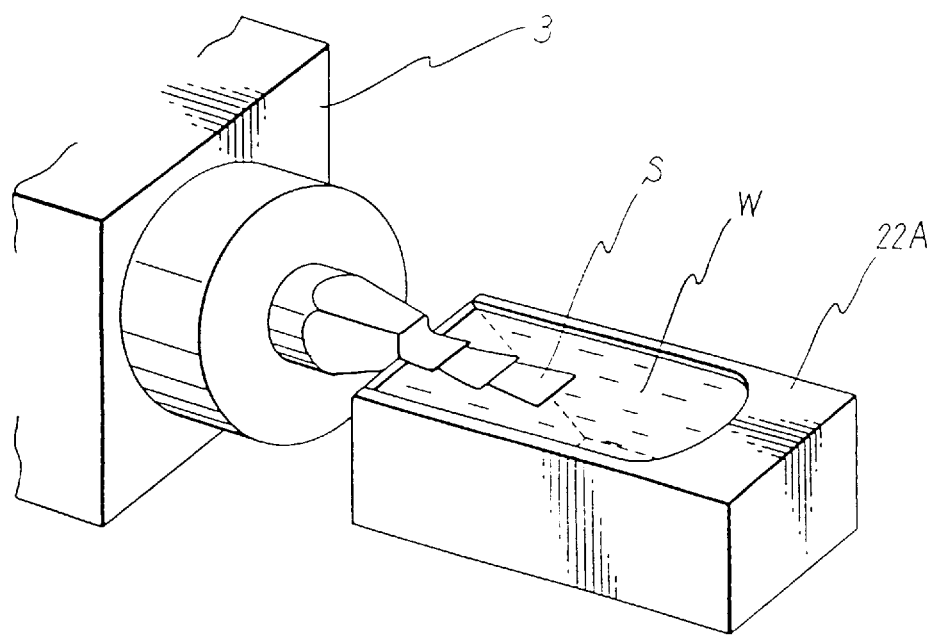
FIG. 4 is a perspective view illustrating collection of an extra-thin section of a sample collecting tank shown in FIG. 1.
Figure 5:
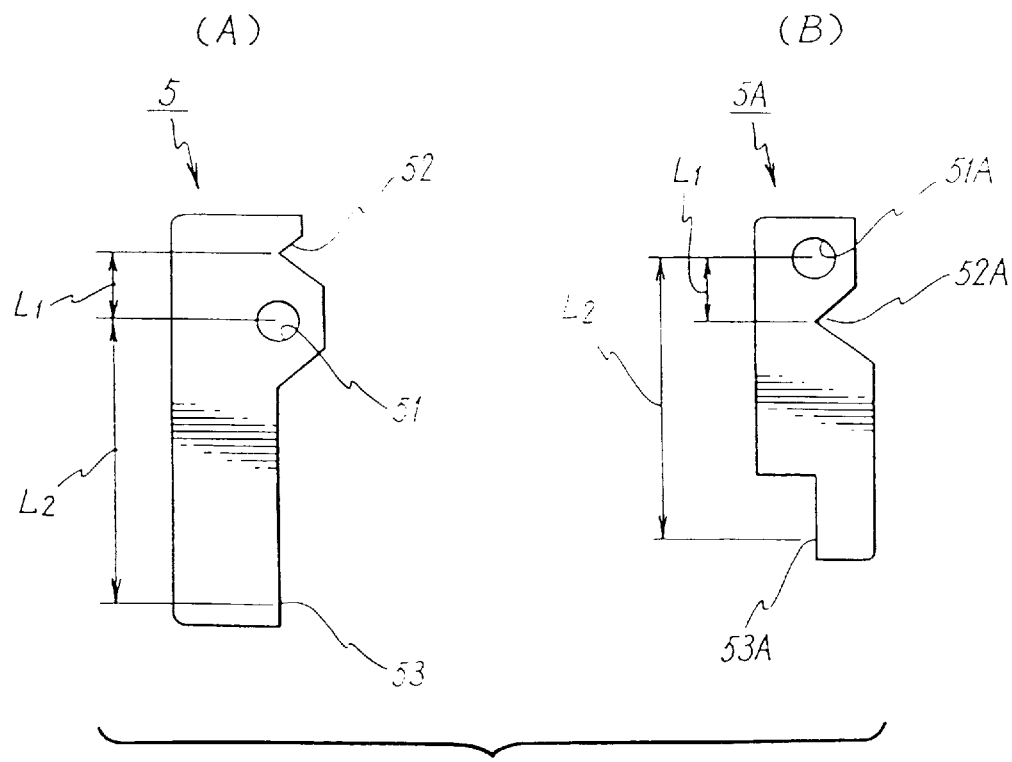
FIG. 5(A) is a front view illustrating a transmission lever shown in FIG. 1.
FIG. 5(B) is a front view illustrating a variation thereof.

The knife holder 22 is formed integrally with the knife 21, and includes a sample collecting tank 22A. Tank 22A includes a distilled water W storing section on the side opposite to the sample S (with the knife in between), and a seat 22B which secures this sample collecting tank 22A on the slant stage 23 with a stop screw 22a. The sample collecting tank 22A collects the sample S when cut as shown in FIG. 4 by causing the sample S to float on the distilled water W.

The holding mechanism 2 includes a knife holder 22 which holds the knife 21 on the upper end thereof, a slant stage 23 which modifies the edge angle of the knife holder 22 around the Y-axis direction (described below) and an X-Y axis stage 24 which moves knife 21 in the X-Y plane.

The slant stage 23 includes a seat 23A secured onto a second traveling carriage 24C of the X-Y axis stage 24. A slant mechanism 23B holds a seat 22B of the knife holder 22 on this seat 23A, and is slidable along a peripheral surface of a cylinder having a center axis in the Y-axis direction relative to the seat 23A. An adjusting knob 23C finely adjusts the inclination angle through sliding of the slant mechanism 23B. The slant stage 23 sets the angle of the knife 21 relative to the sample S.

The X-Y axis stage 24 is a linear stage secured at a position on the right side of the base 1 in FIG. 1. It includes mounting body 24A provided on the base 1, a first traveling carriage 24B slidably mounted on the X-axis direction on this mounting body 24A, and a second traveling carriage 24C connected onto the first traveling carriage 24B and slidable in the Y-axis direction. Roller guides are used for sliding portions.

The position of the first traveling carriage 24B in the X-axis direction is adjusted by the adjusting knob 24D. The first traveling carriage 24B is fixed at an arbitrary position by a set-screw 24a. The position of the second traveling carriage 24C in the Y-axis direction is adjusted by the adjusting knob 24E. The second traveling carriage 24C is fixed by a set-screw 24b at an arbitrary position. More specifically, the X-Y axis stage 24 positions the knife 21 relative to the sample S.

The lever moving mechanism 7 will be described below. The lever moving mechanism 7 includes a pushing member 71 which pushes the contact section 53 of the transmission lever 5 in the X-axis direction through point contact, a first feed mechanism 72 which drives in a direction inclined at a micro-angle ($\theta$) to the Y-axis direction, and a record feed mechanism 73 which drives in a direction inclined at a micro-angle ($-\theta$) in the reverse direction to the first mechanism 72 to the Y-axis direction. The pushing member 71 pushes the transmission lever 5 through cooperation of the first and second feed mechanisms 72 and 73.

The foregoing pushing member 71 has a leading end 71A projecting toward the contact section 53 of the transmission lever 5. This leading end 71A is formed into a spherical or convergent shape. As a result, the pushing member 71 pushes the contact section 53 of the transmission lever 5 as described above with the leading end 71A thereof in the point contact state. More specifically, pressure contact occurs between the leading end 71A and the contact section 53 over a slight area. The point of contact is substantially at the middle of the width of the transmission lever 5 along the Y-axis direction.

Figure 6:
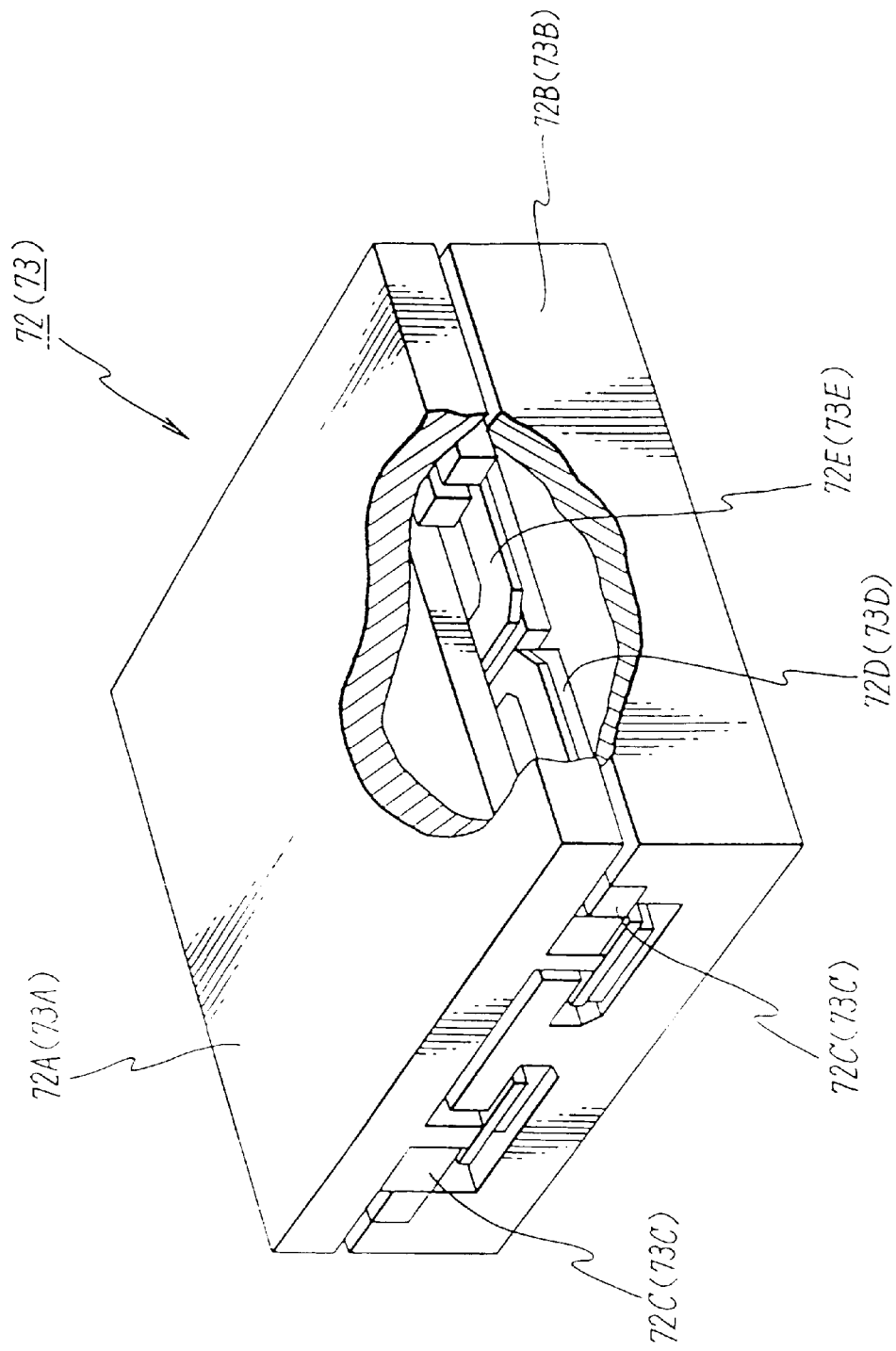
FIG. 6 is a partially cutaway perspective view illustrating one feed mechanism (the other feed mechanism) shown in FIG. 1.

As shown in FIG. 6, each feed mechanism 72 and 73 includes, as shown in FIG. 6, a traveling stage 72A, 73A which moves back and forth in the driving direction, a mounting body 72B, 73B upon which the traveling stage 72A, 73A is mounted, a guide 72C, 73C which guides back and forth movement of the traveling stage 72A, 73A relative to the mounting body 72B, 73B, a magnet 72D, 73D provided on the mounting body 72B, 73B, and a linear motor stage mechanism having a coil 72E, 73E which moves the traveling stage 72A, 73A under the effect of the magnetic field formed with the magnet 72D, 73D.

The foregoing magnet 72D and the coil 72E form a travel imparting mechanism of the first feed mechanism 72, while the magnet 73D and the coil 73E form a travel imparting mechanism for the second feed mechanism 73.

More specifically, the first feed mechanism 72 utilizes the attractive force and repulsive force produced by the magnetic field generated between the coil 72E and the magnet 72D to move the traveling stage 72A relative to the mounting body 72B. Consequently, the traveling stage 72A linearly travels along the guide 72C toward the mounting body 72B. This is also the case with the second feed mechanism 73 and its corresponding elements.

By using the feed mechanisms 72 and 73 for the lever moving mechanism, the following advantages are available. First, it is possible to minimize the effect of backlash and conduct a high accuracy feeding operation by using a magnetic driving force rather than, for example, a ball screw. Second, this mechanism provides a highly linear movement compared with a stepping motor, making it possible to achieve a larger instantaneous torque. Third, the coil has a small inductance, and has an excellent electric response. Fourth, the mechanism is free from magnetic pulsation such as cogging, permitting smooth control at a high accuracy.

In the first feed mechanism 72, the mounting body 72B is provided to the left of the holding mechanism 2 on the base 1 in FIG. 1. The traveling stage 72A on this mounting body 72B is arranged movably along a direction at a micro-angle $+\theta$ to the Y-axis direction by the guide 72C. In the second feed mechanism 73, the mounting body 73B is connected to the traveling stage 72A through a spacer 74. The traveling stage 73A is arranged movably along a direction at a micro-angle $-\theta$ to the Y-axis direction by the guide 73C. The pushing member 71 is secured on the upper surface of the traveling stage 73A, thus permitting back and fourth movement in the X-axis direction by the cooperation of the feed mechanisms 72 and 73.

Figure 7:
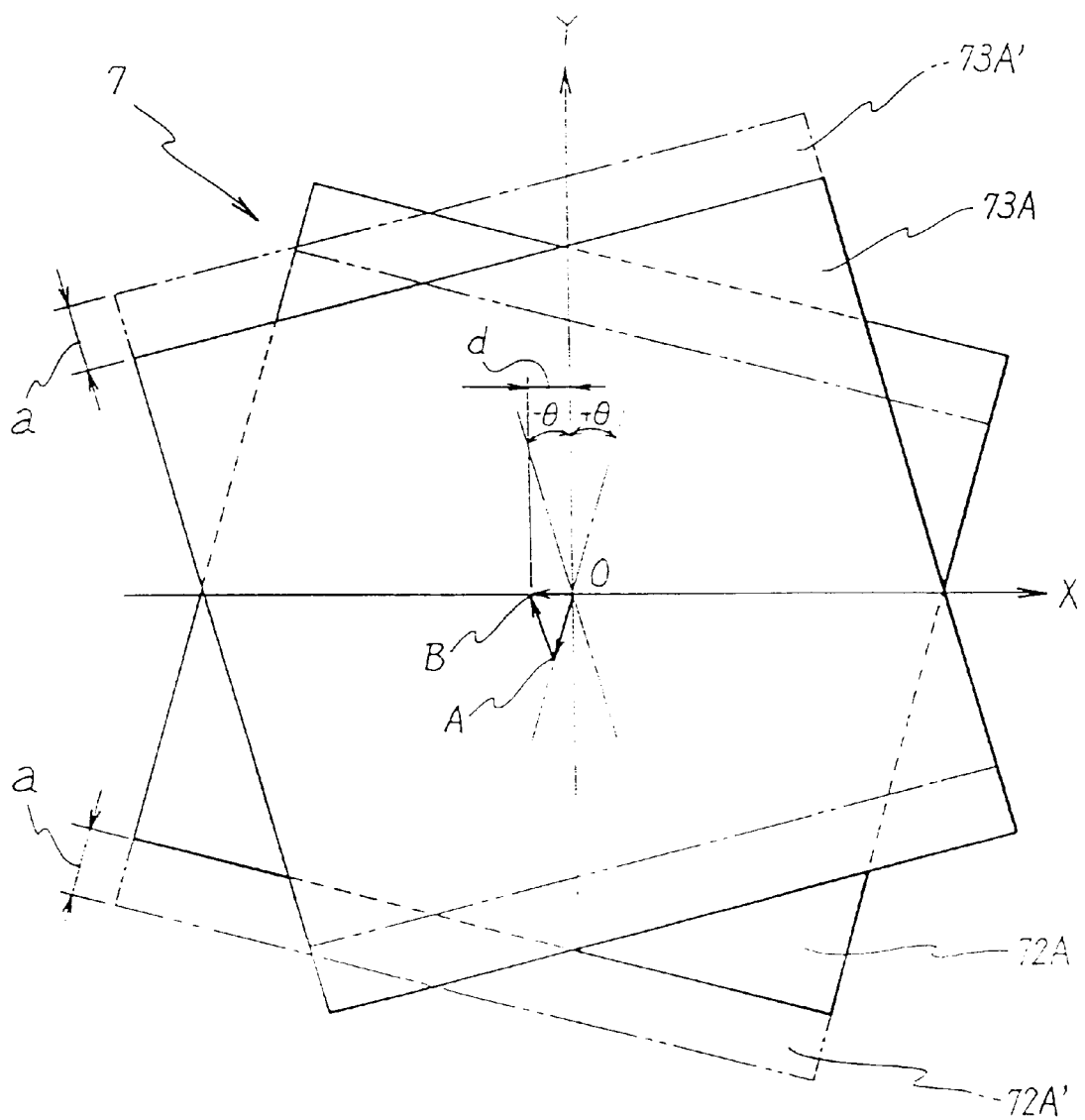
FIG. 7 is a descriptive view illustrating the principle of travel of the lever moving mechanism.

FIG. 7 is a descriptive view illustrating the feeding operation of the lever moving mechanism 7. In the lever moving mechanism 7, the first feed mechanism 72 and the second feed mechanism 73 travel by the same distance a. The traveling stage 72A of the first feed mechanism 72 moves forward by a distance (a) in the direction OA onto the traveling stage 72A'. At this point, the traveling stage 72A moves (a)sin$\theta$ in the X-axis direction. The second feed mechanism 73 moves, on the other hand, by distance (a) in the direction AB to reach the traveling stage 73A'. At this point, the traveling stage 73A moves by (a)sin$\theta$ in the X-axis direction. As a result, the traveling stage 73A of the second feed mechanism 73 has thus made a linear movement by an amount as in $\theta$ in the X-axis direction. In the lever moving mechanism, this amount of displacement 2(a)sin$\theta$ equals the amount of micro-feed d of the pushing member 71.

The crossing angle 2$\theta$ of the first feed mechanism 72 and the second feed mechanism 73 should preferably be set at a small value. For example, when the crossing angle 2$\theta$ is 5°, the amount of micro-feed would be d=0.087(a). It is therefore possible to keep the micro-feed d relative to the pushing member 71 in the X-axis direction to a value less than $\frac{1}{10}$ of the distance (a) of the first feed mechanism 72 and the second feed mechanism 73.

Figure 8:
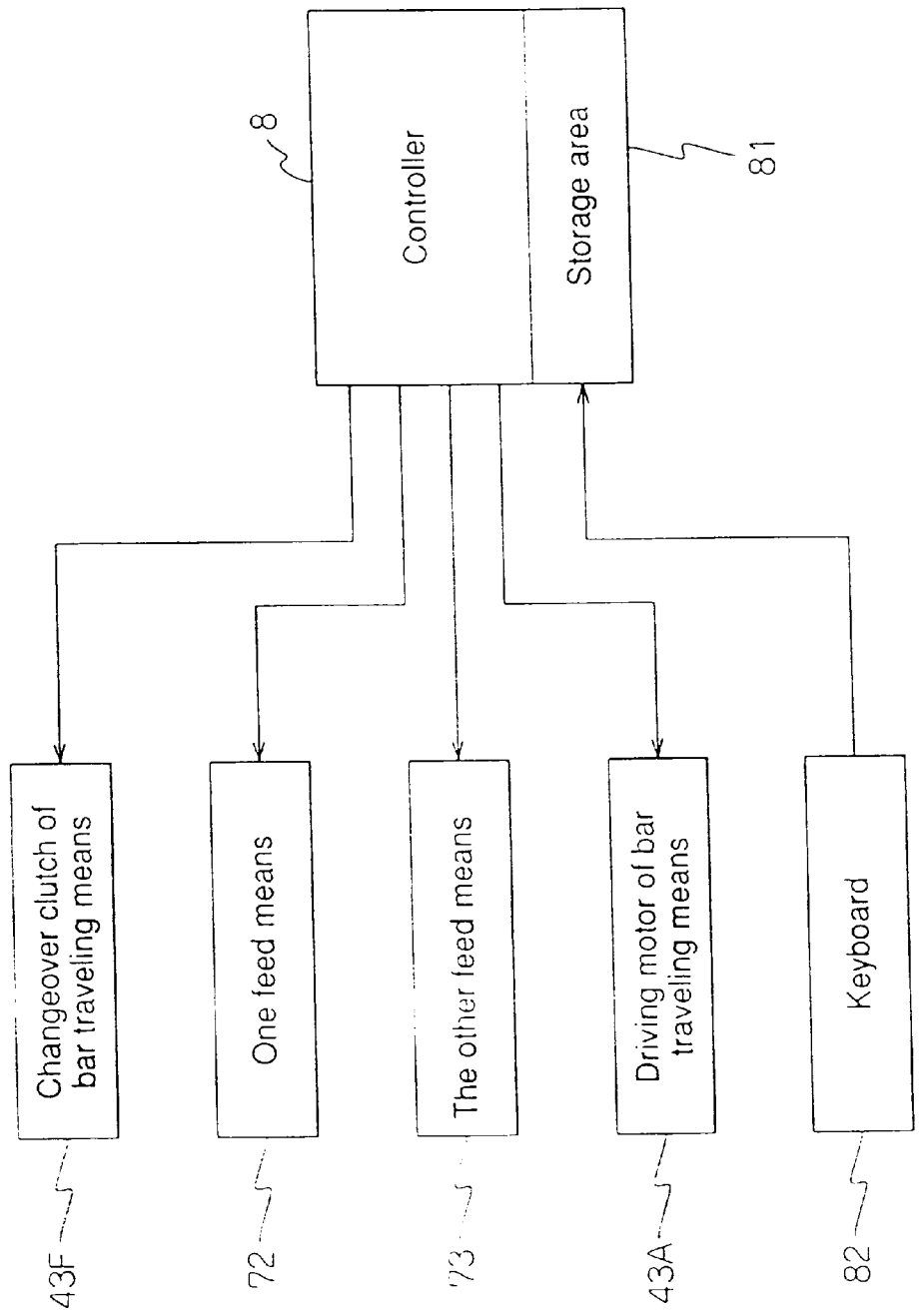
FIG. 8 is a block diagram illustrating a control system of the microtome shown in FIG. 1.
Figure 9:
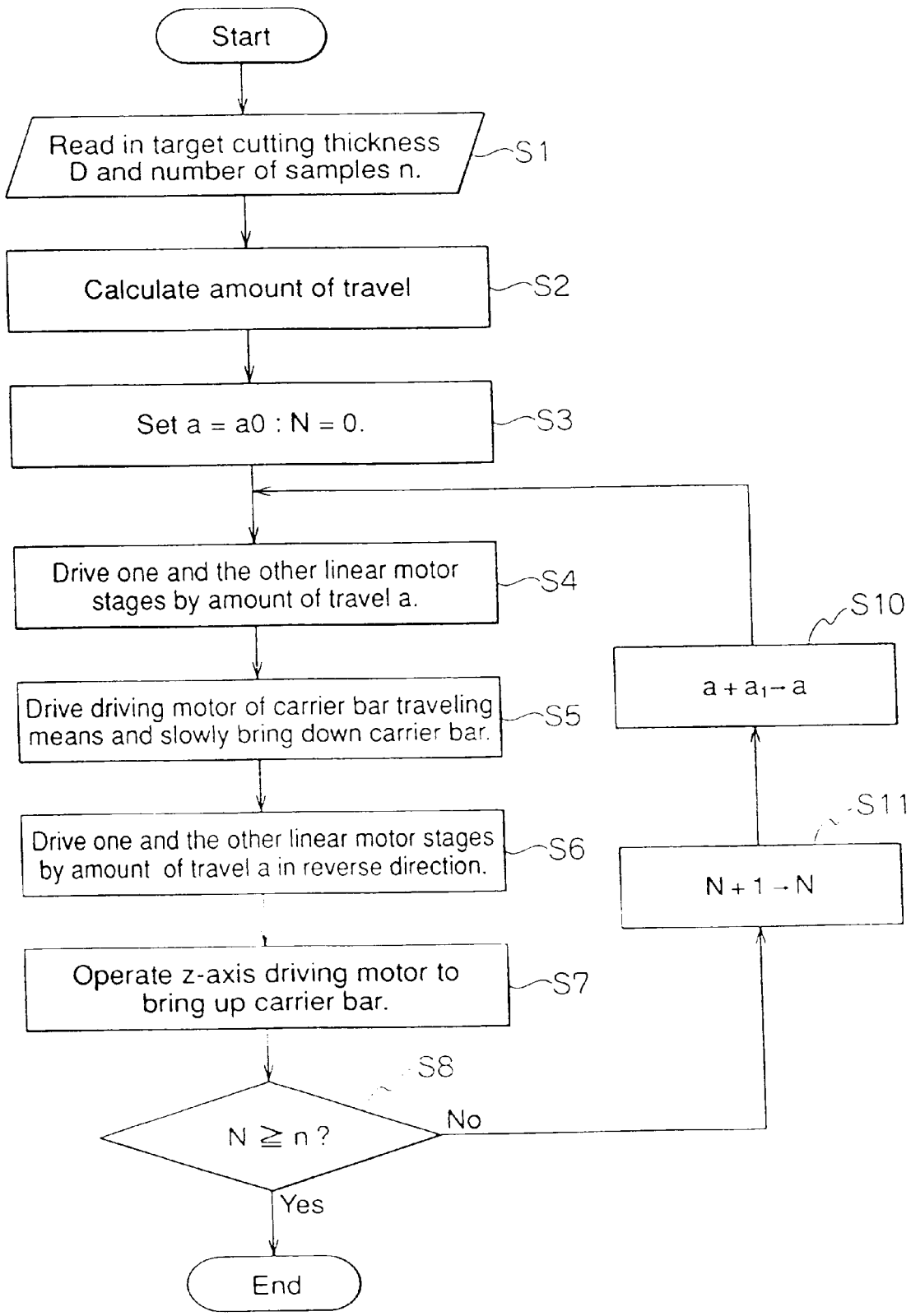
FIG. 9 is a flowchart illustrating operational control during cutting of the microtome shown in FIG. 1.

Now, the controller 8 will be described below with reference to FIG. 8. The controller 8 includes a microcomputer having a built-in operating program for performing operations as shown in FIG. 9 (described later). A storage area 81 stores, through a keyboard 82, a set target cut thickness D of the sample S, a number of samples n, and an initial displacement value a0. The keyboard 82 and various sensors and switches not shown are connected to the input side of the controller 8. A driving motor 43A in a driving mechanism 43 for the first feed mechanism 72, the second feed mechanism 73 and the bar traveling means 4 is connected to the output side thereof As the initial displacement value a0, the position of the first cut of the sample S must be set, irrespective of the amount of microfeed d.

Now, the operations of the microtome 10 having the construction as described above will be described below.

Before operating the microtome 10, the position of knife 21 and the sample S are initialized. More specifically, the knife 21 is moved in the X-axis and Y-axis directions relative to the sample S by the X-Y axis stage 24 of the holding mechanism 2. For the sample S, the transmission lever stage 64 is positioned in the X-axis direction; adjustment is made so that the sample S and the knife 21 are relatively separated in the X-axis direction, and are located substantially at the same position in the Y-axis direction. The relief angle of the knife 21 is adjusted through inclination adjustment of the slant stage 24. The inclination of the sample S is adjusted, on the other hand, by the slant stage 33 in a stage in which the sample S is held by the sample holder 32 of the carrier bar 3.

The subsequent process includes, entering, through a keyboard 82 into the controller 8, an operating instruction for connecting the manual handle 43E and the driving shaft of the driving motor 43A to the changeover clutch 43F of the bar traveling means 4, adjusting the rotation angle of the carrier bar 3 by operating the manual handle 43E so that the sample S and the knife 21 are separated in the X-axis direction and the sample S comes above the knife 21, and then disconnecting the manual handle 43E through the changeover clutch 43F.

The target cutting thickness D of the sample S and the number of samples n are previously entered through the keyboard 82 in step S1. Because the traveling force in the X-axis direction is imparted to the carrier bar 3 through the transmission lever 5, a relationship as expressed by the following formula (1) between the entered target cutting thickness D and the micro-feed distance of the pushing member 71 by the lever moving mechanism 7:

$$d = (L2/L1) \times D \quad (1)$$

The travel distance of the first feed mechanism 72 and the second feed mechanism 73 is calculated from the micro-feed d calculated as above in step S2:

$$a1 = (d/2) \times (\sin\theta)^{-1} \quad (2)$$

In step S3, the initial travel distance a0 is then read out from the storage area 81. The counter N is set at "0", and the initial travel distance a0 is set as the distance (a).

Subsequently, in step S4, the traveling stage 72A of the first feed mechanism 72 and the traveling stage 73A of the second feed mechanism 73 are moved in opposite directions by the travel distance a (initial travel distance a0). As a result, the pushing member 71 pushes the contact section of the transmission lever 5 to displace by 2a0 ($\sin\theta$) in the X-axis direction (causing displacement from right to left in FIG. 1). In response to fluctuation of the transmission lever 5, the carrier bar 3 travels forward to the knife side by 2a0 ($\sin\theta$) (L2/L2) in the X-axis direction against the force of the tension springs 34a.

In step S5, the driving motor 43A to rotate the rotation shaft 41 of the bar traveling means 4 by 180°. Accordingly, the carrier bar 3 slowly lowers the sample holding side thereof in response to the tension of the tension spring 31a. The contact member 31A of the carrier bar 3 and the eccentric cam 42 are always in contact due to the tension of the tension spring 31a, thereby preventing unstable vibration or the like on the sample holding side of the carrier bar 3. Upon contact of the sample S with the edge of the knife 21, a thin section is cut, and the cut thin section floats on the water surface in the sample collecting tank 22A. The thin section cut by the initial cut is not collected since it is only cut for the purpose of forming an end face of the sample S for subsequent cuts.

After the initial cutting of the sample S, the traveling stage 72A of the first feed mechanism 72 and the traveling stage 73A of the second feed mechanism 73 are moved in directions reverse to those in step S4 by a travel distance a (initial travel distance a0) in step S6. By separating the sample S and the knife 21, the sample S does not come into contact with the knife 21 during upward travel of the rotating end of the carrier bar 3.

As a result, in step S7, the driving motor 43A rotates the rotation shaft 41 of the bar traveling means 4 by 180°. The carrier bar 3 slowly raises the sample holding side thereof against the tension of the tension spring 31a. The sample S is moved to a position above the knife 21 (step S7).

At step 8, the controller 8 determines whether or not counter N has reached the number of samples n (step S8). If not, the counter N is increased by one increment in step S9. The travel distance (a) is updated to a+a1 at step S10, whereupon the process is returned to step S4.

In the second and subsequent processes, the feed mechanisms 72 and 73 are driven by the previously calculated travel distance a1 to cut the target cutting thickness D from the leading end of the previously cut sample S. The leading end of the sample S therefore projects from the knife 21 by 2a1 ($\sin\theta$), i.e., by the amount of micro-feed distance d calculated in step S4. Then, the carrier bar 3 is slowly lowered by driving the driving motor 43A. Knife 21 cuts the leading end of the sample S. The cut extra-thin section is collected by causing the same to float on the water surface in the sample collecting tank 22A in step S5.

After downward rotation of the carrier bar 3, the traveling stage 72A of the one feed mechanism 72 and the traveling stage 73A of the other feed mechanism 73 retreat by the travel distance (a) in step S6. The carrier bar 3 rotates upward responsive to the driving motor 43A, and brings the sample S to a position above the knife 21 in step S7.

Extra-thin sections having a thickness D are formed by repeating the above-mentioned cutting operation of the sample S and collecting cut sections in the sample collecting tank 22A.

When it is determined that N=n in step S8, the cutting operation ends.

In the foregoing first embodiment, as described above, the oscillating force of the transmission lever 5 imparted by the lever moving mechanism 7 is induced by the projecting leading end 71A of the pushing member 71 at the point contact. Therefore, compared with a case where the pushing member is connected to the transmission lever, or where they are in the state of face contact, a certain degree of freedom exists which permits mutual oscillation around the contact portion between the pushing member 71 and the transmission lever 5. Vibration occurring in a direction perpendicular to the pushing direction (X-axis direction) (for example, Y-axis or Z-axis direction) does not generally transmit from the pushing member 71 to the transmission lever 5. This insulation from the effect of vibration allows carrier bar 3 to be positioned during cutting with a high degree of accuracy.

In the first embodiment, transmission lever 5 is oscillated by the cooperation of the two feed mechanisms 72 and 73 which drive the lever moving mechanism 7 at a micro-angle $\pm\theta$ to the Y-axis direction. It is therefore possible to position the carrier bar 3 in an amount of feed in micro-units in proportion to $\sin(\pm\theta)$, and hence to increase the accuracy of the cutting operation of the sample S.

More specifically, as compared with the amount of travel a of the first mechanism 72 and the second mechanism 73, it is possible to reduce the amount of micro-feed d by setting a micro-angle $\pm\theta$ and the target cutting thickness D of the sample S in compliance therewith.

When $\theta=7.5°$, for example, the relationship between the amount of travel (a) and the amount of micro-feed d would be d=0.26(a). For $\theta=5.7°$, the relationship between the amount of travel a and the amount of micro-feed d would be d=0.2a. Further, if $\theta=2.5°$ is used, the relationship would be d=0.087(a). The micro-angle $\pm\theta$ may be set even at 2° or 1°.

Therefore, when $\theta=5.7°$ and the first and second mechanism 72 and 73 which serve as a linear motor stage mechanism have a resolution of 100 nm, then the minimum amount of micro-feed d is about 20 nm. Because of the construction in which the carrier bar 3 is positioned through the transmission lever, it would be possible to manufacture extra-thin sections of the sample S having a thickness of from 4 to 5 nm.

When the micro-angle $\pm\theta$ is $\theta=5.7°$, on the other hand, if the feed mechanisms 72 and 73 have a resolution of 10 nm, it is theoretically possible to manufacture thin sections having a thickness within a range of from 0.4 to 0.5 nm. When θ=2.5° is used for the micro-angle ±θ, and the feed mechanisms have a resolution of 100 nm, then the minimum amount of micro-feed d would be about 8.7 nm, producing extra-thin sections of the sample S theoretically having a thickness within a range of from 1.7 to 2.2 nm. As is clear from the above examples, it is possible to easily manufacture extra-thin sections of a sample S by setting the micro-angle ±θ at an appropriate value.

Because the first feed mechanism 72 and the second feed mechanism 73 drive in a direction crossing the Y-axis direction at a slight inclination angle, a high holding force can be kept against the pushing force in the X-axis direction. More specifically, upon impinging of the sample S on the knife 21, the pushing member 71 is held at current position against the reaction force in the X-axis direction received through the carrier bar 3 and the transmission lever 5. This prevents the sample S from escaping and eliminates a shear of the amount of micro-feed d. Thus, the sample S is cut accurately to the target cutting thickness D.

As described above, because feed mechanism 72 and 73 serve as a linear motor stage mechanism, backlash or the like is minimized. The feed operation has a higher accuracy compared with a mechanical driving source, such as a ball screw. Compared with a stepping motor, it provides more uniform current and thrust, generates a larger instantaneous torque relative to ratings, uses a small coil and inductance, has an excellent electric response, and does not experience magnetic pulsation (such as cogging).

In the lever moving mechanism 7, the mounting body 73B of the second feed mechanism 73 is mounted on the traveling stage 72A of the first feed mechanism 72. The pushing member 71 is secured onto the traveling stage 73A of the feed mechanism 73 placed thereabove, thereby imparting force in the pushing direction by the cooperation of the two feed mechanism 72 and 73 without requiring a complicated motion transmitting mechanism. The number of parts is therefore reduced.

The position of the transmission lever 5 between the lever moving mechanism 7 and the carrier bar 3 allows it to absorb vibration produced when driving lever moving mechanism 7. It is therefore possible to reduce the effect of vibration on the carrier bar 3.

The distance L1 between the holding section 51 and the transmitting section 52 of the transmission lever 5 is set at a value smaller than the distance L2 between the holding section 52 and the contact section 53. As a result, the displacement transmitted from the transmission lever 5 to the carrier bar 3 is smaller than the displacement applied by the pushing member 7 to the transmission lever 5. The carrier bar 3 is thus positioned in smaller micro-units than the lever moving mechanism 7. By setting a large L2/L1 value (within a reasonable range taking into account the equipment size and the occupied space in the interior), cutting operations occur with a higher accuracy.

Since the support plate 6 has side walls 61 and 62 and an erection stand 63, the transmission lever 5 is supported on the both sides in the Y-axis direction through the transmission lever stage 64. The transmission lever 5 is thus held in a stable state against external forces, such as rotation of the carrier bar 3 and the pushing force given by the lever moving mechanism 7. This minimizes cutting error.

The erection stand 63 is located above the lever moving mechanism 7. Consequently, the lever moving mechanism 7, the support plate 6 and the transmission lever 5 are aligned along a vertical line on the base 1. It is therefore possible to save the required space and downsize the apparatus as a whole.

The microtome of the present invention uses the slightest contact area between the lever moving mechanism and the transmission lever, as described above. Compared to a case where the lever moving mechanism and the transmission lever are connected together, or where the pushing force is imparted through a wide contact surface, there is an available degree of freedom for producing oscillation around the contact portion between the lever moving mechanism and the transmission lever. For example, vibration in a direction perpendicular to the pushing direction does not transmit from one to the other such that the carrier bar can be positioned at a higher accuracy.

Because the transmission lever is between the lever moving mechanism and the carrier bar, vibration transmits from the transmission lever to the side of the support plate holding the transmission lever. This further reduces the effect of vibration.

According to an embodiment of the present invention, the transmission lever oscillates by the cooperation of the two feed mechanisms 72 and 73 to drive the lever moving mechanism in a direction at a slight angle to the perpendicular of the pushing direction of the pushing member. It is therefore possible to position the carrier bar in micro-units proportional to a value shown by the sin of each of these slight angles, and thus to achieve a further higher accuracy for cutting the sample.

According to another embodiment of the present invention, the first and second feed mechanisms 72 and 73 serve as a linear motor stage mechanism which drives under the effect of magnetic field produced in a magnet and a coil. Compared with a combination of mechanical elements, such as a ball screw, it is possible to exclude the effects of the assembly accuracy of individual elements and the play necessary (for example, the effect of backlash), to perform the feed operation.

According to the present invention, the mounting body of the second mechanism is placed on the traveling stage of the first feed mechanism, and the pushing member is secured onto the traveling stage of the upper feed mechanism. By so doing, it is possible to impart force in the pushing direction by the cooperation of the two feed mechanism without intervention of a complicated force transmitting mechanism between the feed mechanism and the pushing member, improving productivity through reduction of the number of necessary parts. Because it is not necessary to provide a complicated transmitting mechanism, the probability of an error in the travel distance between the feed mechanism and the pushing member is reduced, improving the positioning accuracy of the carrier bar.

In the first embodiment described above, a linear motor stage mechanism is adopted as the first feed mechanism 72 and the second feed mechanism 73. Pushing force may, however, be imparted by the pushing member 71 by any other technique. For example, even the ball screw mechanism as described above may be adopted as the first feed mechanism and the second feed mechanism only if an elastic spring giving pushing force or tensile force along the pushing direction between the ball screw holding side and the ball screw driving side. Even with such a construction, it is possible to provide a microtome having a higher accuracy than the prior art.

In the above-mentioned embodiment, production is possible by means of a conventional ball screw mechanism type microtome, and it is possible to improve the cutting accuracy and exclude vibration without wasting conventional products.

The structure of the engagement portion of the edge 34 of the carrier bar 3 and the transmitting section 52 of the transmission lever 5 shown in the first embodiment is not limited specifically to the above-mentioned shape, but may be any structure which is not susceptible to the effect of the working accuracy of the individual components during rotation of the carrier bar 3. For example, it may be a structure in which a cylindrical recipient member is provided in the Y-axis direction on the transmission lever 5 side, and a forked structure opening toward the transmission lever 5 side is provided on the leading end side of the edge 34 of the carrier bar 3. The recipient member of the transmission lever 5 is inserted into this fork. In this case, the contact state of the fork structure and the recipient member is effectively maintained by the tension springs 34a. Therefore, the carrier bar 3 can freely rotate around the recipient member of the transmission lever 5, and occurrence of an error during rotation is effectively prevented.

In this embodiment, pushing operation is accomplished through point contact between the pushing member 71 and the contact section 53 of the transmission lever 5. This may also be conducted with a construction in which the pushing member 71 and the contact section 53 of the transmission lever 5 come into mutual contact through line contact by changing the shape of the leading end of the pushing member 71.

For the foregoing holding mechanism 2 and the carrier bar 3, the construction may be such that the sample S is mounted on the holding mechanism 2 and the knife 21 is mounted on the carrier bar 3.

More specifically, a sample holder 32 is provided on the upper portion of the holding mechanism 2 and a cylindrical sample S is mounted in the X-axis direction. The leading end thereof is opposite to the knife 21 held by the carrier bar 3, in this sample holder 32. A knife holder 22 holding the knife held by a rotating end of the bar body 31 is provided on the carrier bar 3.

In the foregoing embodiment shown in FIG. 1, upon cutting the sample S, the sample S held at the rotating leading end of the carrier bar 3 is positioned above the knife 21, and cut when the carrier bar 3 moves down. Since the knife 21 is held on the carrier bar 3 side in this embodiment, the leading end of the carrier bar 3 is positioned below the sample S before cutting, and the sample S is cut upon moving the carrier bar 3 up.

In addition, if, when cutting the sample S, the leading end of the carrier bar 3 is below the sample S, the carrier bar 3 travels forward by a distance equal to the target cutting thickness D toward the holding mechanism 2 by the action of the lever moving mechanism 7. Rearward movement occurs after upward rotation of the carrier bar 3.

Also for the above-mentioned construction, as described above, it is possible to obtain the same effect as the microtome 10 shown in FIG. 1 described above.

Figure 10:
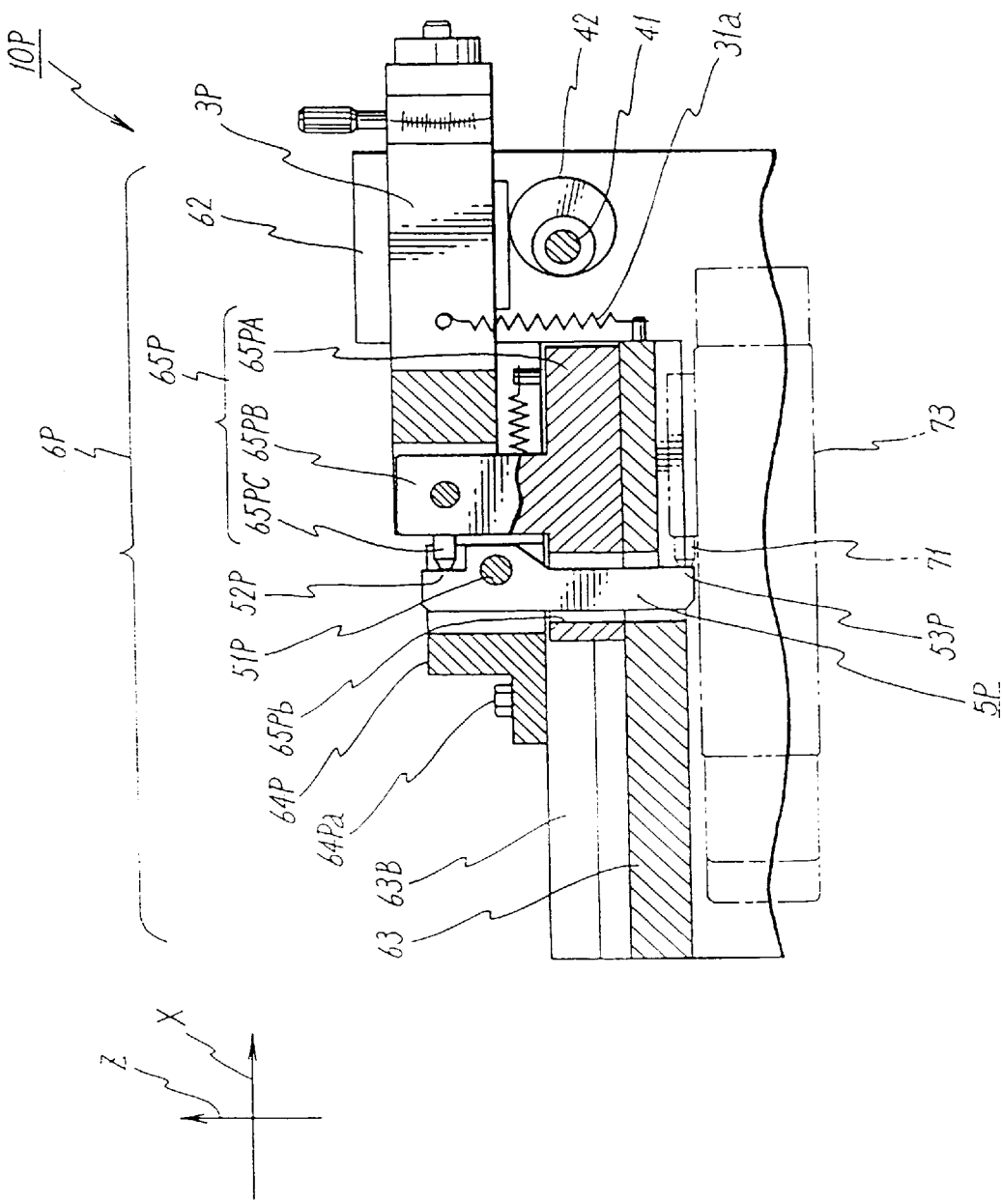
FIG. 10 is a partially cutaway front view illustrating a second embodiment of the present invention.
Figure 11:
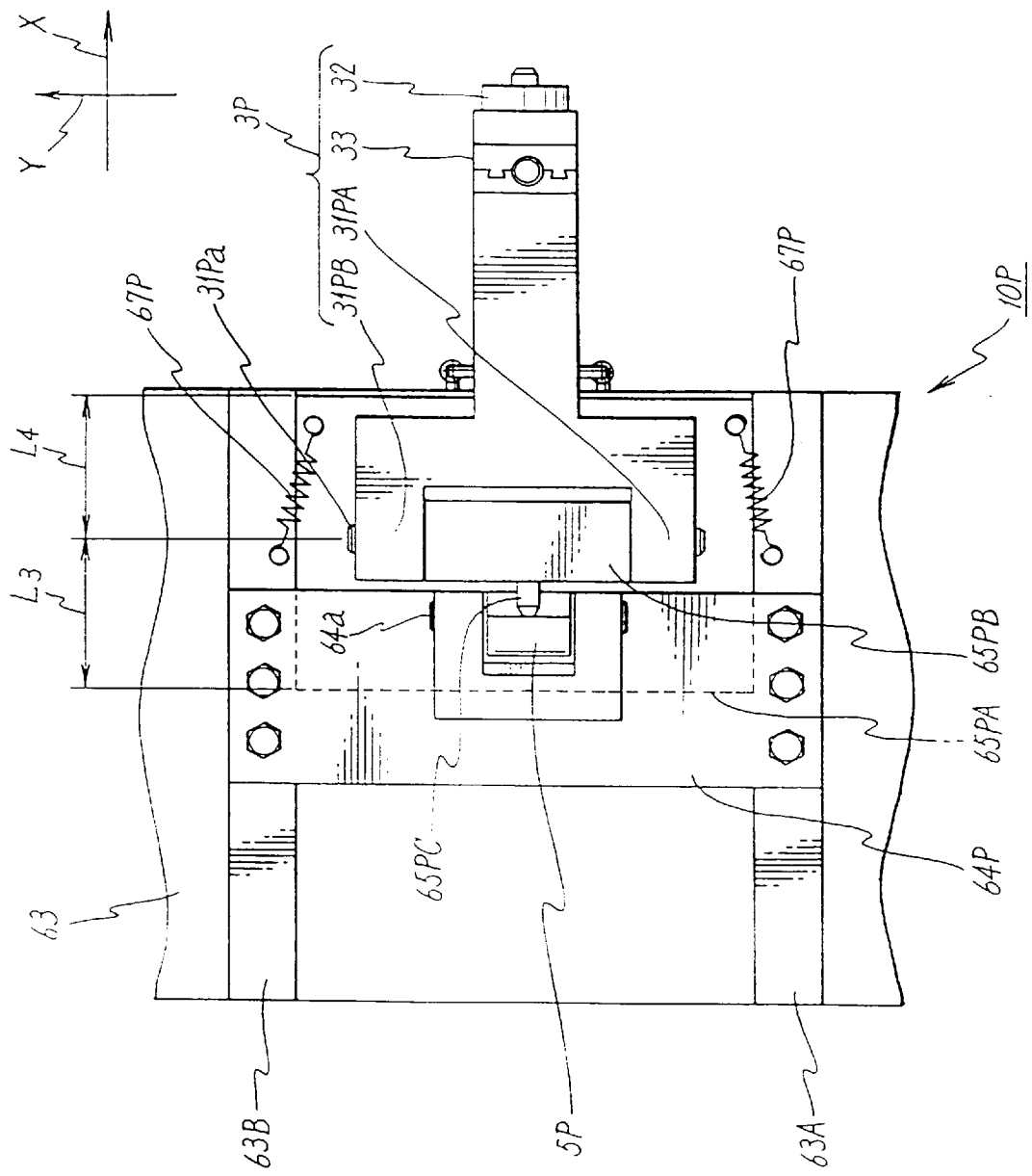
FIG. 11 is a partially omitted front view of the microtome shown in FIG. 10.
Figure 12:
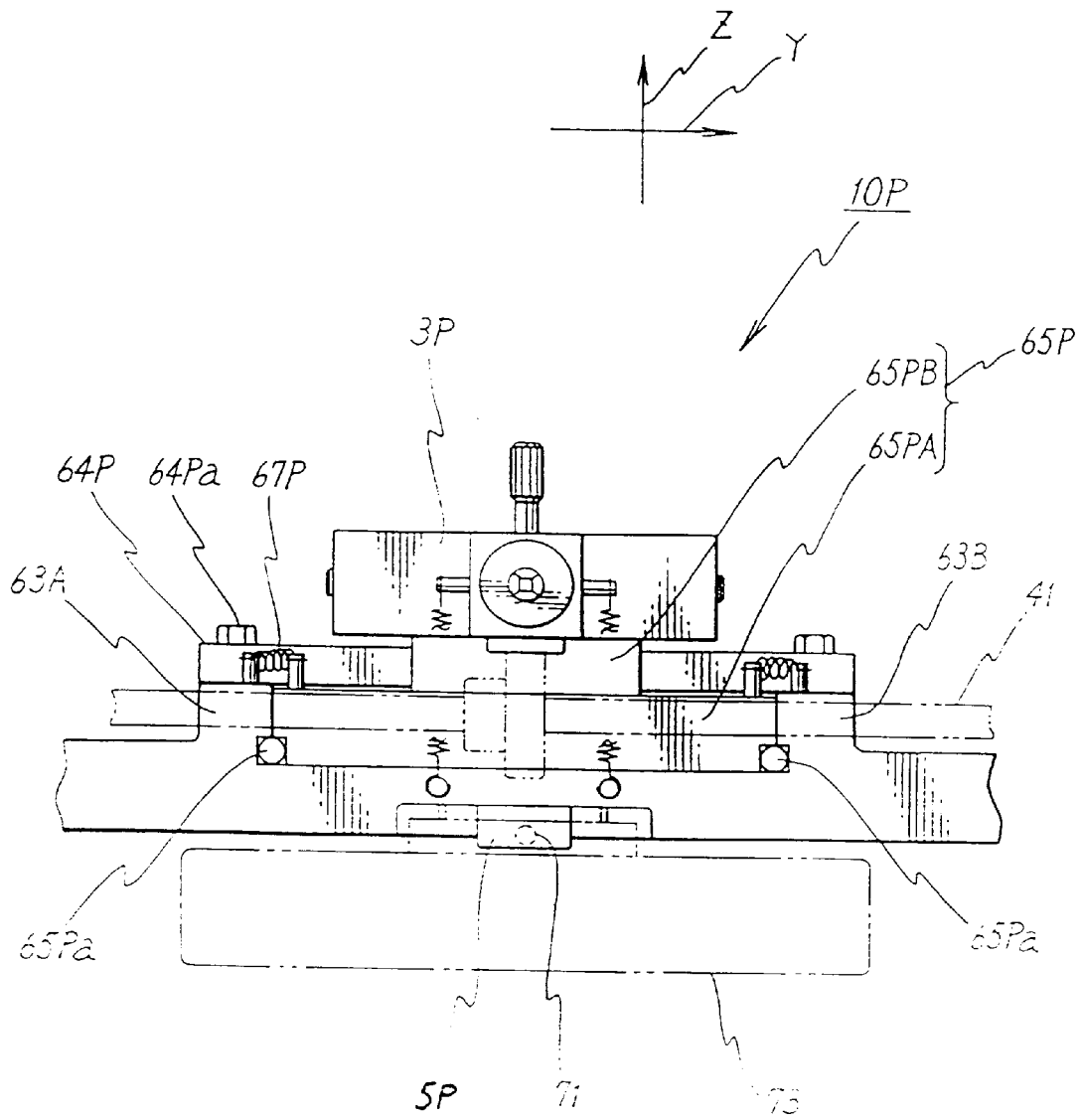
FIG. 12 is a partially cutaway side view of the microtome shown in FIG. 10.

A second embodiment of the present invention is illustrated in FIGS. 10 to 12. A microtome 10P representing this second embodiment is different from the foregoing microtome in that the carrier bar 3, the transmission lever 5 and the support plate 6 are different in structure, with all the other conditions being the same. The identical parts to those for the microtome 10 are indicated by the same reference numerals, the description therefore being omitted.

The support plate 6P of this microtome 10P has side walls 61 and 62, an erection stand 63 and guide rails 63A and 63B identical with those of the above-mentioned support plate 6, but not a transmission lever stage 64. The transmission lever 5P is installed between guide rails 63A and 63B, and is held rotatably through a supporting shaft 64a on a transmission lever holder 64P secured with a fixing bolt 64Pa on the guide rails 63A and 63B. Consequently, while rough positioning of the transmission lever 5P in the X-axis direction before cutting cannot be conducted, it is possible to perform positioning in the X-axis direction by an X-Y axis stage 24 on the knife side, thus giving no direct influence on cutting operation.

A carrier bar stage 65P reciprocating in the X-axis direction is provided along the guide rails 63A and 63B between these guide rails 63A and 63B on the erection stand 63. This carrier bar stage 65P rotatably holds the carrier bar 3P and has a function of transmitting the pushing force from the transmission lever 5P through the carrier bar stage 65P to the carrier bar 3. The carrier bar stage 65P includes a rectangular flat body 65PA arranged between the guide rails 63A and 63B, a carrier bar holder 65PB installed on the body 65PA, and a projection 65PC receiving the transmitted pushing force in the X-axis direction from the transmission lever 5P.

The rectangular body 65PA is arranged with a parallel pair of sides along the X axis, and the other pair along the Y axis. Since it is engaged through the roller guide 65Pa with a guide rails 63A and 63B, it produces smooth reciprocation in the X-axis direction at a high accuracy without play or shear.

A through-hole 65Pb is provided near the carrier bar holder 65PB in this body 65PA, and the transmission lever 5P is held by the above-mentioned transmission holder 64P in a state inserted into this through-hole 65Pb. This through-hole 65Pb is set at such a size that rooms are provided before and after the X axis relative to the transmission lever 5P. As a result, the transmission lever 5P does not form an obstacle, and the carrier bar stage 65P can reciprocate in X-axis direction.

Tension springs 67P are stretched between the body 65PA and the individual guide rails 63A and 63B, respectively. Consequently, the body 65PA is subjected to a tension in a direction in which a projection 65PC described later comes into pressure-contact with the transmission lever 5P.

The carrier bar holder 65PB is a square-pole member installed vertically at a position serving as the point of intersection (i.e., the central portion) of two diagonal lines of the body 65PA, and rotatably holds the carrier bar 3P holding the sample S. The carrier bar holder 65PB has a through-hole (not shown) in the Y-axis direction for insertion of the supporting shaft 31Pa which engages with fork portions 31PA and 31PB of the carrier bar 3P described later, and rotatably holds the supporting shaft 31Pa by a bearing (not shown) or the like provided in the insertion hole.

The forked portions 31PA and 31PB of the carrier bar 3 are connected to the ends of the supporting shaft 31Pa, respectively. Carrier bar 3 can thus rotate relative to the carrier bar holder 65PB around the supporting shaft 31Pa.

This supporting shaft 35Pa is located at equal distances from the both ends in the X-axis direction of the above-mentioned body 65PA (L3=L4 in FIG. 11). The middle portion of the supporting shaft 35Pa in the axial direction is located above the central portion of the above-mentioned body 65PA. More specifically, the supporting shaft 35Pa is positioned just at the center of the body 65PA, and the carrier bar 3P is supported through this supporting shaft 35Pa. The carrier bar stage 65P is therefore well balanced for both the X-axis and the Y-axis directions, permitting smooth travel on the erection stand 63.

A projection 65PC projecting toward the transmitting section 52P of the transmission lever 5P described later is provided on the surface of the carrier bar holder 65PB opposite to the transmission lever 5P. The tip of this projection 65PC is formed into a spherical or convergent shape, imparting the pushing force from the transmission lever 5P through point contact of the tip of the projection 65PC with the transmission section 52 of the transmission lever 5P. Even when vibration occurs, only the transmission lever 5P vibrates around the point contact portion thereof. The pushing force is transmitted in the X-axis direction to the projection 65PC side with minimal vibration.

The transmission lever 5P will now be described. As in the transmission lever 5 described above, the transmission lever 5P has a holding section 51P, a transmitting section 52P and a contact section 53P. Among these sections, the holding section 51P is a through-hole into which a supporting shaft 64a, rotatably held in the Y-axis direction on a transmission lever stage 64P of the support plate 6P, is to be inserted. The transmission lever 5P is rotatably held by the transmission lever stage 64P around the holding section 51P. The tip of the projection 65PC of the abovementioned carrier bar stage 65P comes into contact with the transmitting section 52P. The pushing member 71 of the lever moving mechanism 7 comes into contact with the contact section 53P. As a result, the transmission lever 5P imparts the pushing force in microunits, given by the lever moving mechanism 7 to the carrier bar 3P through the carrier bar stage 65P, as a travel operation in the X-axis direction.

The holding section 51P, the transmitting section 52P, and the contact section 53P described above are arranged along a line, and the distance between the contact section 53P and the holding section 51P is set at a plurality of times (preferably four to five times) the distance between the holding section 51P and the transmitting section 52P. The transmission lever 5P has the same functions as the transmission lever 5.

The foregoing transmitting section 52P and the contact section 53P are located substantially in the middle of the Y-axis direction width of the transmission lever 5P. This maintains contact between the projection 65PC and the pushing member 71 in good balance. For example, a V-shaped groove or a slight recess may be provided in the transmitting section 52P and the contact section 53P to maintain a holding state by excluding a positional shear or the like of the projection 65PC and the pushing member 71.

The carrier bar 3P will now be described. As in the carrier bar 3 described previously, the carrier bar 3P has a sample holder 32 and a slant stage 33 at the leading end, and the other end (the left end in FIG. 11) is branched into a fork shape. More specifically, the carrier bar 3P is formed into substantially a Y shape as a whole. Two legs of the forked portion 31PA and 31PB are arranged on both sides of the carrier bar holding section 65P in the Y-axis direction. The carrier bar holding section 65PB of the carrier bar stage 65P is in between. The two legs are individually connected to the both ends of the above-mentioned supporting shaft 31PA. Consequently, the carrier bar 3P is rotatably held by the carrier bar stage 65P around the supporting shaft 31PA.

This carrier bar 3P is formed into a substantially Y shape to ensure a large width on the fulcrum side, and the supporting shaft 31PA is directed in the Y-axis direction. The carrier bar 3P is therefore stable in the Y-axis direction, which inhibits vibration generation.

In the microtome 10P having the construction as described above, the carrier bar 3P, when traveling in the X-axis direction, travels together with the carrier bar stage 65P. More specifically, when the sample S held by the carrier bar 3P is brought closer to the knife 21 side, the contact section 53P of the transmission lever 5P is pushed through the pushing member 71 of the lever moving mechanism 7, and the entire transmission lever 5P is oscillated. Along with the oscillation of the transmission lever 5P, the projection 65PC is pushed by the transmitting section 52P, such that the entire carrier bar stage 65P travels in the X-axis direction to the right in FIG. 10. At the same time, the carrier bar 3P held by the carrier bar stage 65P travels in the same direction.

When the sample S held by the carrier bar 3P is separated from the knife 21, the pushing member 71 of the lever moving mechanism 7 retreats in the reverse direction to the pushing action. The body 65PA of the carrier bar stage 65P, always receiving tension of the tension springs 67P, travels as a whole toward the left in FIG. 10 upon release of the projection 65PC from the pushing state from the transmitting section 52B of the transmission lever 5P. Accordingly, the carrier bar 3P held by the carrier bar stage 65P travels in the same direction.

Operations of the individual components are performed in the same manner as in the microtome 10.

In this second embodiment, as described above, the carrier bar 3P is held by the support plate 6 fixed to the base 1. The carrier bar 3 is therefore held in a stable state. Even during travel or rotation of the carrier bar 3P in the X-axis direction, it is barely susceptible to the influence of vibration resulting from the other components of the apparatus or an external cause. As a result, positional shear or a positioning error is minimized, and an extra-thin section can be cut with a high accuracy.

Because the carrier bar stage 65P holds the carrier bar 3P at the central portion of the carrier bar stage 65P, it is easy to maintain a balanced state in the X-axis direction as well as in the Y-axis direction. When the carrier bar stage 65P travels in the X-axis direction, or the carrier bar 3P rotates, the carrier bar stage 65P is barely susceptible to vibration in the X-axis direction or in the Y-axis direction. As a result, the effect of vibration is reduced.

According to the microtome of the present invention, as described above, the carrier bar is held by the support plate fixed to the base. The carrier bar is therefore held in a stable state. Even during travel or rotation of the carrier bar in the X-axis direction, it is barely susceptible to vibration resulting from any other component of the apparatus or an external cause.

What is claimed is:

1. A microtome, comprising:
   a base;
   a knife;
   a knife holder, mounted on said base, that holds said knife;
   a carrier bar having a leading end which can support a sample in proximity to said knife, and a trailing end having a wedge shaped edge which acts as a fulcrum about which said carrier bar can pivot;
   a bar traveling mechanism that supports said carrier bar and for pivoting said carrier bar about said wedge shaped edge;
   a lever moving mechanism;
   a transmission lever having a first end in contact with said lever moving mechanism and a second end having a recess which engages said wedge shaped edge of said trailing end;
   a support plate, mounted on said base, which rotatably supports said transmission lever; and
   at least one tension spring which pulls said carrier bar toward said transmission lever;
   wherein said lever moving mechanism moves said transmission lever to move said leading edge of said carrier bar toward and away from said knife.

2. A microtome according to claim 1, wherein said lever moving mechanism includes a pushing member having a sharp leading end in contact with said transmission lever.

3. A microtome according to claim 2, wherein said lever moving mechanism comprises:

a first feed system that drives said pushing member in a direction at a first angle to a perpendicular of the pushing direction of the pushing member; and a second feed system that drives said pushing member in a direction at a second angle, equal to a negative of said first angle about the perpendicular of the pushing direction;

wherein said pushing member in moved in said pushing direction through cooperation of said first feed system and said second feed system.

4. A microtome according to claim wherein 3, said first feed system and said second feed system respectively comprise:

a reciprocally moving traveling stage;

a mounting body upon which said traveling stage is mounted;

a guide which guides movement of said traveling stage relative to said mounting body; and a linear motor, provided between said traveling stage and said mounting body, which moves said traveling stage.

5. A microtome according to claim 4, further comprising a control section which controls said linear motor, said control section including a drive amount calculating system that calculates drive parameters of said linear motor from the first and second angles based on a target thickness of a sample to be cut by said knife.

6. A microtome according to claim 5, wherein said wedge-shaped edge of said carrier bar has a larger width in a direction perpendicular to a feed direction of said carrier bar than a width of the leading end of said carrier bar; and a width of said recess of said transmission lever is larger than said width of the leading end of said carrier bar, and smaller than said width of said wedge-shaped edge of said carrier bar.

7. A microtome according to claim 6, wherein said at least one tension spring includes two springs, mounted on both sides of said leading end of said carrier bar; and the edge of said carrier bar has a straight and sharp tip which is pressed against the recess of said transmission lever by said tension spring.

8. A microtome according to claim 1, wherein said bar traveling mechanism includes a rotation shaft rotatably installed on a side wall of said support plate, an eccentric cam fixedly attached to said rotation shaft, said eccentric cam deviates from a center axis of said rotation shaft such that an outer periphery of said cam contacts said carrier bar, and a motor that rotates said rotation shaft.

9. A microtome according to claim 8, wherein another tension spring pulls said carrier bar toward said eccentric cam.

10. A microtome according to claim 1, wherein said support plate comprises:

two side walls, upright on said base with said lever moving mechanism positioned therebetween;

an erection stand provided above said moving mechanism and between said two side walls; and said transmission lever being mounted on said erection stand.

11. A microtome according to claim 1, wherein a stage for carrier bar which rotatably holds said carrier bar, and transmits pushing force from said transmission lever to said carrier bar is simultaneously provided for said carrier bar.

* * * * *